United States Patent
Marretti

(10) Patent No.: US 11,039,903 B2
(45) Date of Patent: Jun. 22, 2021

(54) SUPPORT, POSITIONING AND HANDLING DEVICE FOR SURGICAL EQUIPMENT AND INSTRUMENTS

(71) Applicant: Giuseppe Marretti, Montale (IT)

(72) Inventor: Giuseppe Marretti, Montale (IT)

( * ) Notice: Subject to any disclaimer, the term of this patent is extended or adjusted under 35 U.S.C. 154(b) by 181 days.

(21) Appl. No.: 16/435,432

(22) Filed: Jun. 7, 2019

(65) Prior Publication Data
US 2019/0380808 A1 Dec. 19, 2019

(30) Foreign Application Priority Data
Jun. 15, 2018 (EP) ..................................... 18178102

(51) Int. Cl.
| | |
|---|---|
| *A61B 90/50* | (2016.01) |
| *A61B 34/30* | (2016.01) |
| *A61B 34/00* | (2016.01) |
| *A61B 17/16* | (2006.01) |

(52) U.S. Cl.
CPC .............. *A61B 90/50* (2016.02); *A61B 34/30* (2016.02); *A61B 17/1675* (2013.01); *A61B 34/70* (2016.02)

(58) Field of Classification Search
CPC ..... A61B 17/1675; A61B 34/30; A61B 34/70; A61B 90/11; A61B 90/50; A61B 2017/00477; A61B 2090/061; A61B 2090/508; A61B 2090/067
See application file for complete search history.

(56) References Cited

U.S. PATENT DOCUMENTS

| | | | |
|---|---|---|---|
| 4,686,997 A | | 8/1987 | Oloff |
| 4,953,540 A | * | 9/1990 | Ray et al. .......... A61B 17/0293 |
| | | | 600/233 |
| 5,984,866 A | * | 11/1999 | Rullo ..................... A61B 17/02 |
| | | | 600/227 |

(Continued)

FOREIGN PATENT DOCUMENTS

| | | |
|---|---|---|
| EP | 2893898 A1 | 6/2015 |
| EP | 3273877 B1 | 1/2018 |

(Continued)

OTHER PUBLICATIONS

EPO First Examination Report, EP181781022, dated May 27, 2019.
(Continued)

*Primary Examiner* — Jocelin C Tanner
(74) *Attorney, Agent, or Firm* — Nancy J. Flint, Attorney At Law, P.A.; Nancy J. Flint, Esq.

(57) ABSTRACT

A support, positioning and handling device for surgical equipment and instruments such as, for instance, drills, comparators, or resection guides, for arthroplasty operations, in particular for distal femur and/or proximal tibia resection. The device comprises a plurality of linear guides and an angular guide which make it possible to determine the position and angle of operation of the surgical instrument, while also allowing to move it with an extreme accuracy. The plurality of guides guarantees a three-dimensional displacement and inclination of a tool-holder turret, which holds an instrument-holder arm which features an engagement surface with the instrument inclined by a predetermined amount, in order to vary the inclination of the latter.
The device allows to perform the arthroplasty surgery without having to drill intramedullary holes, reducing trauma to the patient.

14 Claims, 14 Drawing Sheets

(56) References Cited

U.S. PATENT DOCUMENTS

| | | | |
|---|---|---|---|
| 6,231,526 B1 | 5/2001 | Taylor | |
| 2007/0073136 A1 | 3/2007 | Metzger | |
| 2009/0163928 A1* | 6/2009 | Schena | A61G 13/04 |
| | | | 606/130 |
| 2017/0000320 A1* | 1/2017 | Wilson | A61B 46/10 |
| 2018/0028387 A1* | 2/2018 | Yellin | A61B 90/50 |

FOREIGN PATENT DOCUMENTS

| | | |
|---|---|---|
| WO | 0030548 A1 | 6/2000 |
| WO | 2009092059 A2 | 7/2009 |
| WO | 2013084221 A1 | 6/2013 |
| WO | 2016154606 A1 | 9/2016 |

OTHER PUBLICATIONS

NexGen Complete Knee Solution, Epicondylar Instrumentation Surgical Technique for Legacy Posterior Stabilized Knees.
Zimmer Persona the Personalized Knee System Surgical Technique, Rev. 8, MC0000121281, Jun. 20, 2014, Zimmer, Inc.
European Search Report, EP 18 17 8102, dated Dec. 7, 2018.
EPO Written Opinion, EP 18 178 102.2.

* cited by examiner

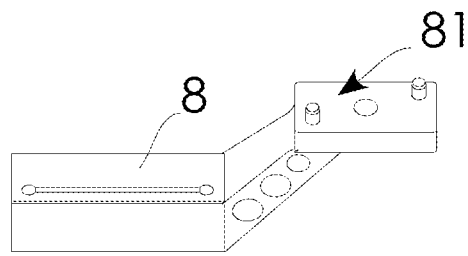
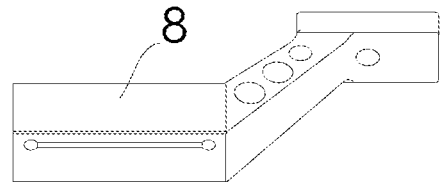
FIG. 18  FIG. 19
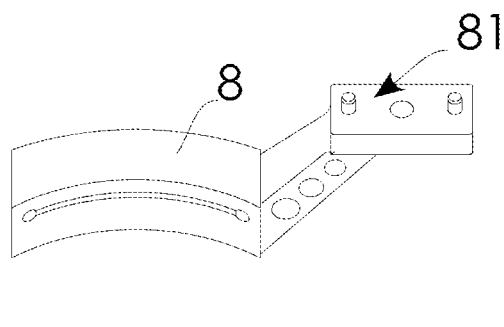
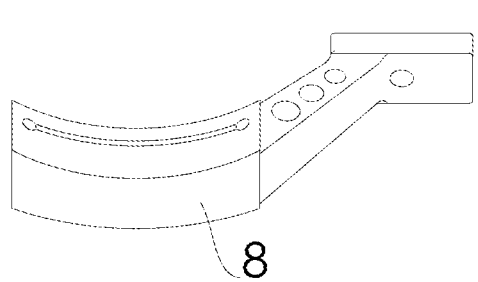
FIG. 20  FIG. 21
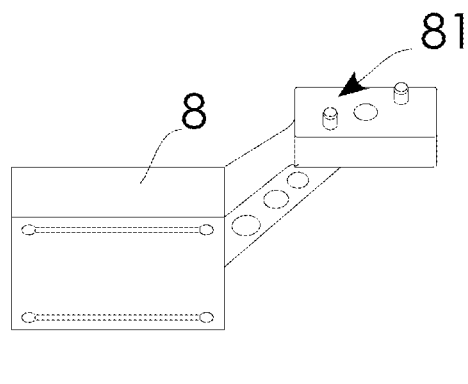
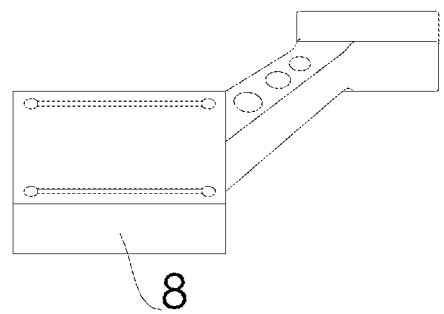
FIG. 22  FIG. 23

SUPPORT, POSITIONING AND HANDLING DEVICE FOR SURGICAL EQUIPMENT AND INSTRUMENTS

TECHNICAL FIELD

The present invention belongs to the sector of the apparatuses used in orthopedic surgery and specifically in total knee prosthesis operations. In particular, the invention refers to a device for correctly positioning and guiding surgical equipment and instruments, such as, for instance, resection masks, feelers, and drills, during a total knee arthroplasty.

PRESENT STATUS OF THE ART

Knee prosthetic surgery includes resection of the distal portion of femur and of the proximal portion of the tibia in order to replace them with artificial prostheses, which replicate those parts of the bone which have been removed. In order for such operation to be successful, it is very important to make sure that the individual prosthetic components are aligned along precise axes determined by articular biomechanics. Any misalignments might result in an early mobilization of the implantation, and consequently in speeding up tear and wear of the prosthesis, which implies serious risks of major functional limitations; for this reason, the surgeon's action is assisted by guiding systems of various types.

Apparatuses have been developed which help surgeons, to be used both in the preliminary step, in order to identify reference points or relevant areas of femur and tibia, and in the subsequent operation step, in order to perform cutting, milling, or other processings.

Almost all failures in arthroplasty operations are to be imputed to misalignments of the prostheses; at present, for instance, in order to guide the cutting, by hand, of the distal part of the femur and the cutting of the proximal part of the tibia, the blade of the oscillating saw is guided by a resection mask and it is fundamental that this mask be perpendicular to the mechanical axis of the femur which, from the center of the hip, goes through the knee and subsequently goes towards the astragalus bone in the foot.

In general, it is necessary to preliminarily define a reference point on the patient's leg in order to perform an operation correctly; having identified this point, its coordinates are stored, in order for them to be used in the subsequent steps of the operation; it is necessary to keep this reference during the complete course of the operation. Today an endomedullary alignment system is often used, which has the anatomic axis of the femur as a reference. According to this method, the angle formed between the mechanical axis and the anatomic axis of the femur is measured, then femoral resection is performed by using devices equipped with a goniometer, in order to try to reproduce the same angle.

Another critical step in the endomedullary system consists of the perforation to be made in order to position the alignment rod, which shall be performed close to the condyloid incisure. An incorrect position of the hole results in an inaccurate resection.

Other operation techniques are described, for instance, in document "*Le protesi di ginocchio*" (knee prostheses), ISBN 9788871419541, or in document "*La protesi di ginocchio di prime impianto*" (first implantation knee prosthesis), ISBN 9788847003798.

Document EP 3273877 (A1) discloses an apparatus for performing knee arthroplasty operations, which comprises devices used to define the positions and the alignment of resections. The same patent application also discloses a method for using the apparatus, a rather complex one, which, on the other hand, does not guarantee accurate alignments, while requiring a plurality of elements to be secured onto the patient's body.

Document US 2007073136 (A1) applies augmented reality to knee arthroplasty operations to display the sequence of the actions conducted on a patient directly on anatomic images thereof, which are obtained by way of tomography or radiography. The system guides the surgeon in the course of the operation, by three-dimensionally tracing the position of the surgical instrument. It is necessary to calibrate the tracing system and/or the use of anatomic models to relate the representations to the real anatomy of the patient, and expensive and complex hardware apparatus and software are also necessary. This system allows to quickly displace the position of the surgical instrument, but the latter is not equipped with any guides and helps as required to keep the determined orientation over time. Also, the surgical instrument is handled by way of handlers operated by the surgeon manually or semiautomatically.

Document U.S. Pat. No. 6,231,526 (B1) discloses a handler for surgical operations conducted with the help of augmented reality; the use of such handler entails a more complex and more expensive operating room and calls for a special ability to surgeons in order to manage the numerous degrees of freedom of the complete system. Also, measuring errors tend to propagate. A need is thus felt for a device capable of making arthroplasty operations easier, such that a surgeon can use it to position the surgical equipment and instruments according to the desired positions and angles, while guaranteeing a high accuracy, by accurately measuring every displacement and simultaneously minimizing the total number of movements necessary to perform a surgical operation and reducing the number of errors inherent to the manual positioning of the resection masks and of the other surgical pieces of equipment.

OBJECTS AND SUMMARY OF THE INVENTION

A first object of the present invention is thus to provide an apparatus capable of positioning and handling surgical equipment and instruments in a simple and intuitive manner, while reducing the displacements necessary to perform the operation and making endomedullary perforations unnecessary. In particular, the present invention aims at positioning the resection masks in a mechanical manner rather than in a manual manner, and solves the problem of helping surgeons in identifying the reference anatomic point with respect to which the surgical pieces of equipment and instruments are positioned, thus reducing misalignments.

A second object of the invention is to permanently guarantee a high accuracy, while offering the possibility of promptly varying positioning.

A last but not least object of the present invention is to reduce the number of elements, such as masks or templates, that are provisionally secured onto the patient's body in the course of an operation by using disposable special nails and screws, thus obtaining advantages both economically-wise and in terms of reduced traumas caused to patients.

A further object of the present invention is to reduce the risk of errors in preparing the device and in assembling the surgical instruments.

These objects and others which will be apparent from reading the present text are achieved by way of an innovative support, positioning, and handling device for surgical instruments, such as drills, comparators, or resection guides.

The device according to the present patent application comprises a horizontal bench, transversal with respect to the longitudinal axis of the operating table and vertically sliding with respect to the latter.

A plate slides on the transversal bench which a board is slidingly coupled with according to a longitudinal axis; a reclining guide is rotationally coupled with the board and a turret supporting an instrument-holder arm slides thereon.

The slidings and rotation of the reclining guide are driven by the operator, usually by way of worm screws manually operated by way of handwheels; graduated scales and nonii or electronic position transducers are used to identify the individual positions accurately; means are also provided for locking the movable element in intermediate positions. The slidings of the transversal bench, plate, and longitudinal guide make it possible to identify the reference point, and the inclination of the surgical instrument can be determined by way of the rotation of the reclining guide with respect to the longitudinal board.

In an advantageous embodiment, the device comprises a plurality of instrument-holder arms, which differ from each other in the different inclinations of the coupling surface between the arm and the surgical instruments, so as to modify the inclination of the latter. The reclining guide being rotatable and the coupling between the arm and the surgical instrument make it possible to easily manage two degrees of freedom of the latter.

According to a preferred embodiment, mutual engagement means are provided between the tool-holder turret and the instrument-holder arms, and between the latter and the surgical instruments; the mutual engagement means are configured so as to prevent wrong couplings from taking place between the parties.

Figure 1:
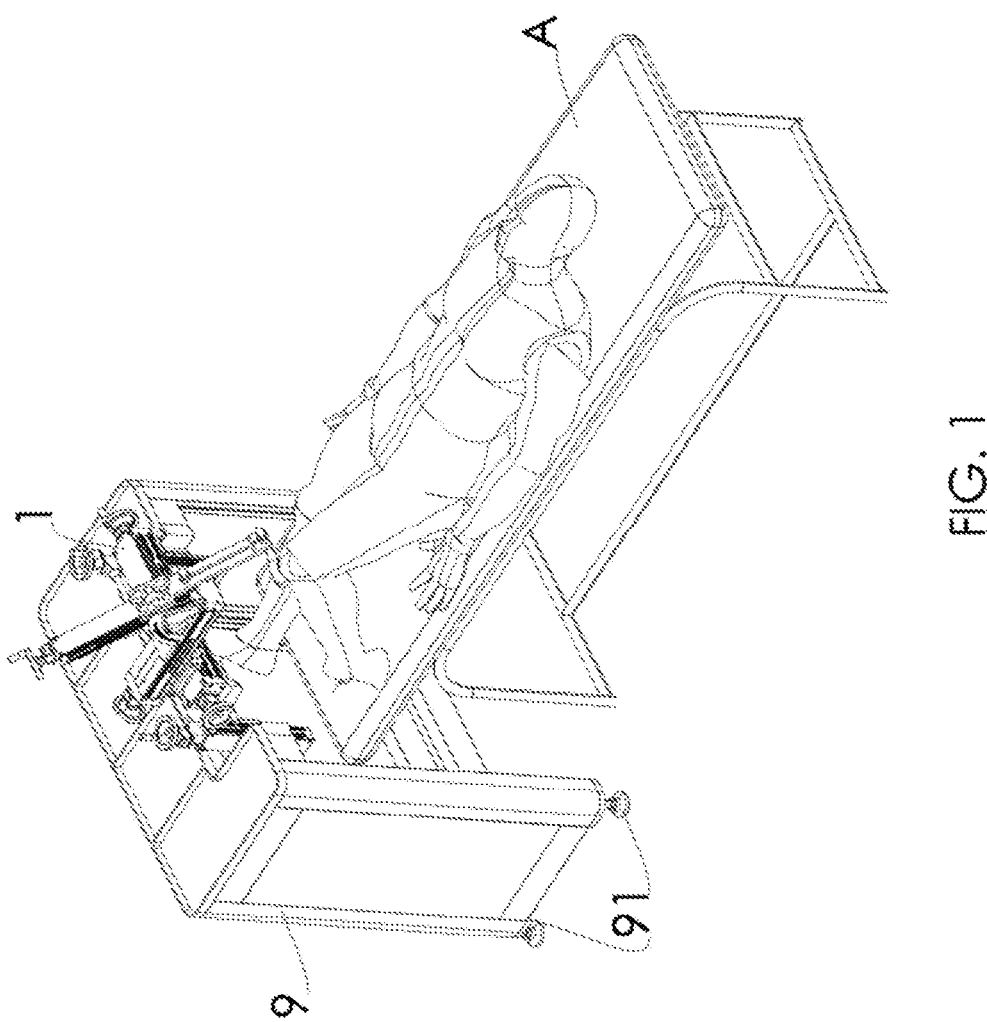
FIG. 1 shows an axonometric top view of an embodiment of the invention, which shows the horizontal longitudinal plane (A) of the operating table on which a patient lays supine, his/her leg to be operated on being held bent. In the figure the horizontal transversal linear bench (1) is separated from the operating table and is supported by a base (9) equipped with adjustable feet (91), by adjusting which the bench (1) can be levelled.
Figure 2:
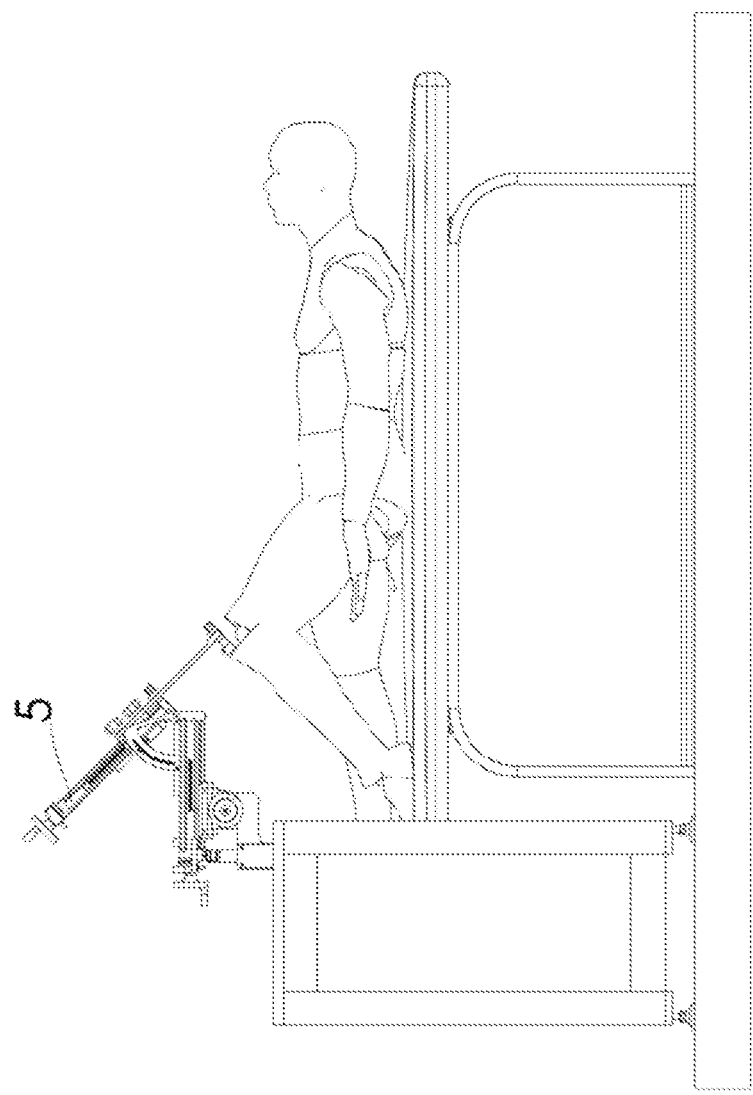
FIG. 2 shows a side view of the device depicted in the previous figure, and specifically highlights the reclining guide (5).
Figure 3:
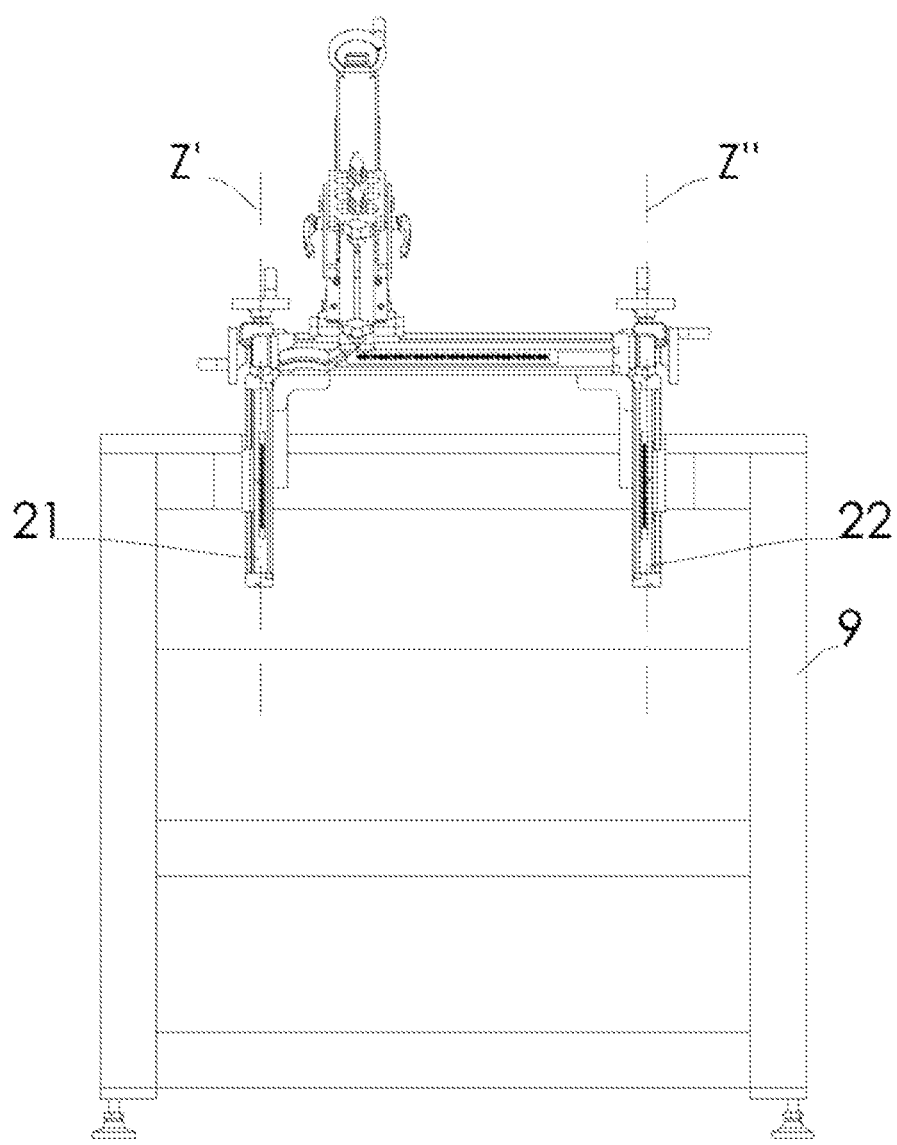
FIG. 3 shows a front view of the device depicted in FIG. 1, from the patient's point of view. In the configuration here shown, the ends of the bench (1) slide with respect to the base (9) along the vertical axes (Z' and Z"); in the solution here shown, the bench slides vertically by way of two linear guides (21, 22).
Figure 4:
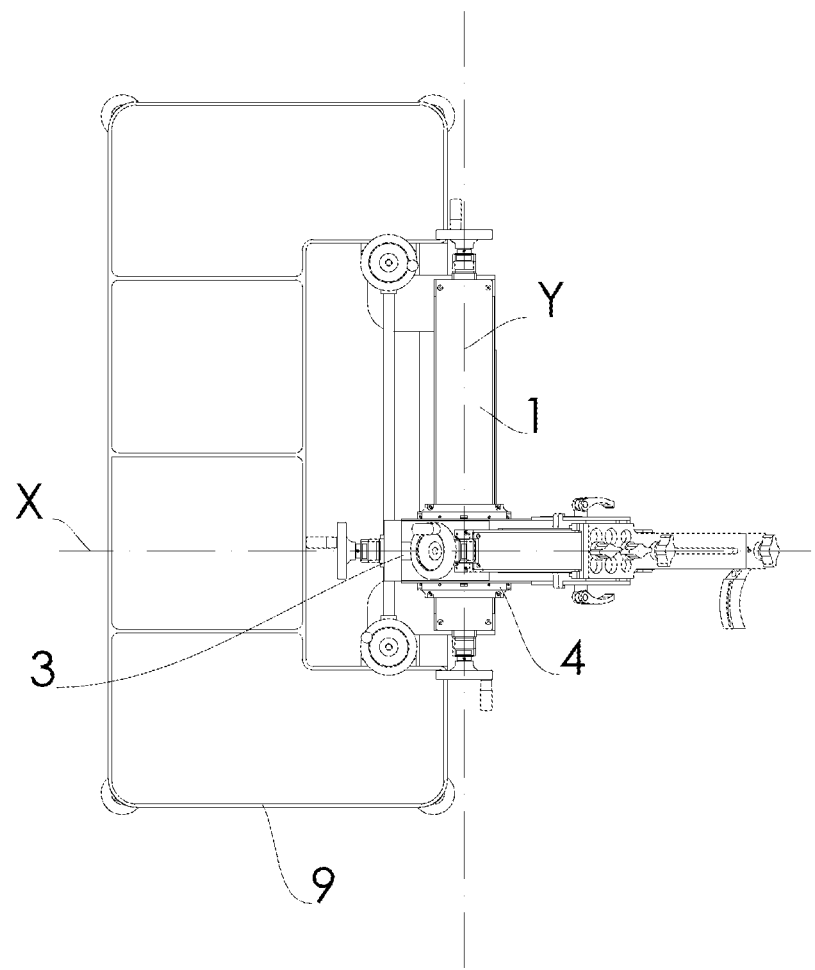
FIG. 4 shows a top view of the device depicted in FIG. 1, and specifically the longitudinal axis (X) along which the longitudinal board (3) slides with respect to the plate (4) and the transversal axis (Y) according to which the plate (4) slides with respect to the horizontal transversal linear bench (1).
Figure 5:
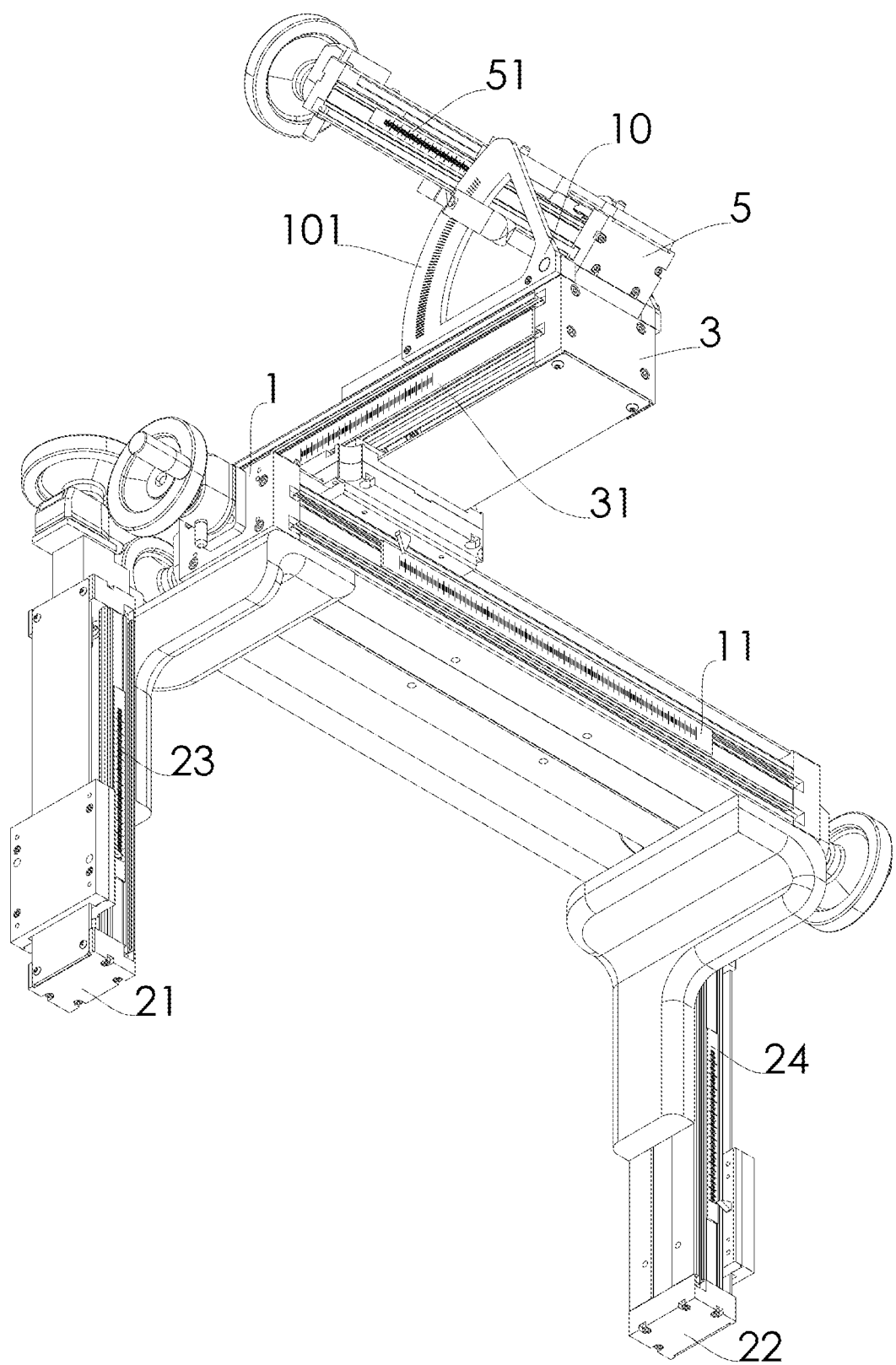
FIG. 5 shows a partial bottom axonometric view of the device depicted in FIG. 1, and specifically the graduated scale (23, 24) of the vertical linear guides (21, 22), the graduated scale (11) of the horizontal transversal linear bench (1), the graduated scale (31) of the board (3), the graduated scale (51) measuring the progress of the reclining guide (5), and the graduated scale (101) of the angular guide (10).
Figure 6:
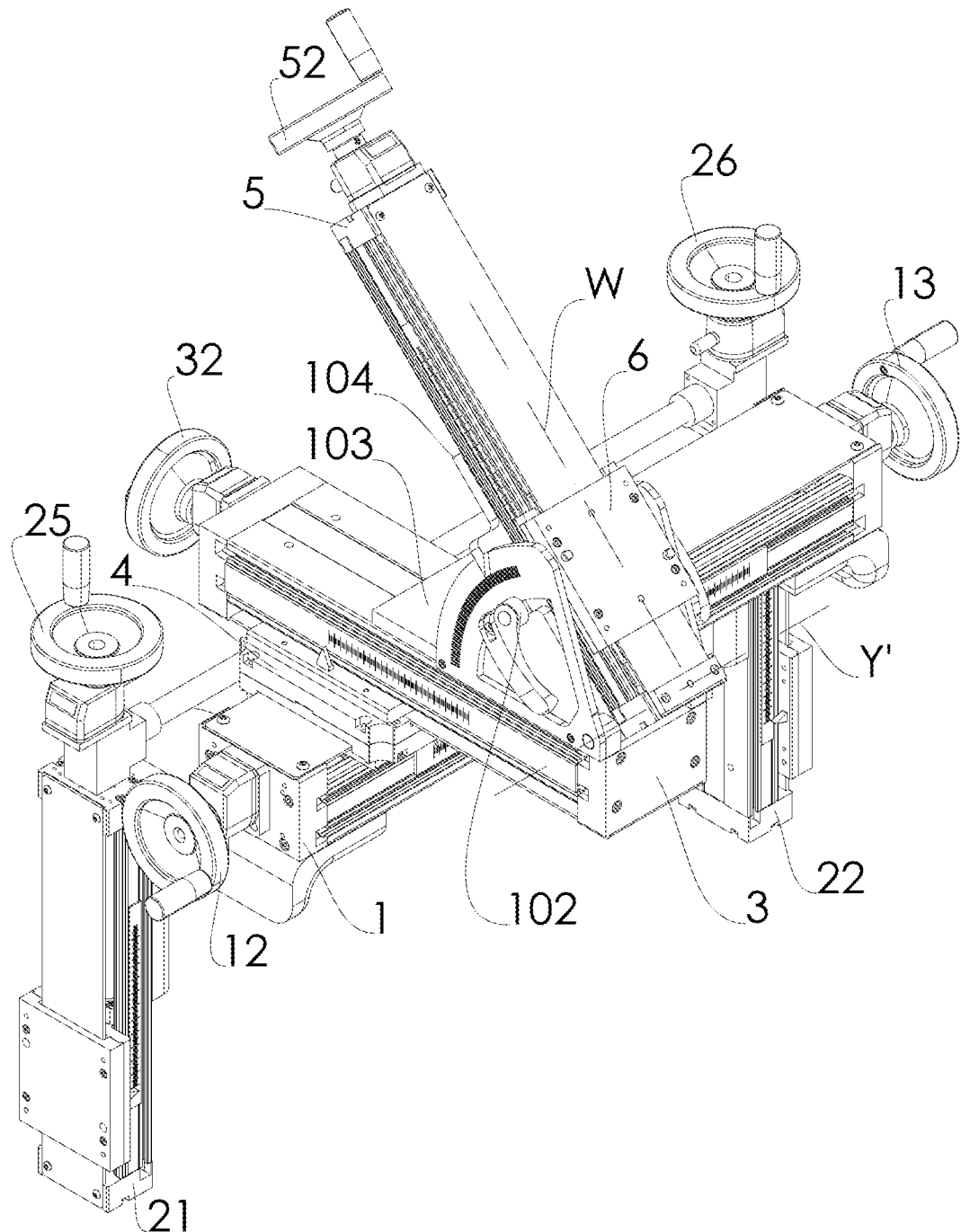
FIG. 6 shows a partial top axonometric view of the previous figure. This figure highlights the handwheels (25, 26) used to make the vertical linear guides (21, 22) move forward, the handwheels (12, 13) used to make the bench (1) move forward, the handwheel (32) used to make the board (3) move forward, the pivot (102) used to lock the angular guide (10), and the handwheel (52) used to make the reclining guide (5) move forward.

The figure also shows the fixed portion (103) of the angular guide (10), integral with the board (3) and with the angular graduated scale (101), and the movable portion (104) rotationally connected to the fixed portion according to a transversal axis of rotation (Y'), said movable portion (104) being integrally connected to said reclining guide (5).

Figure 7:
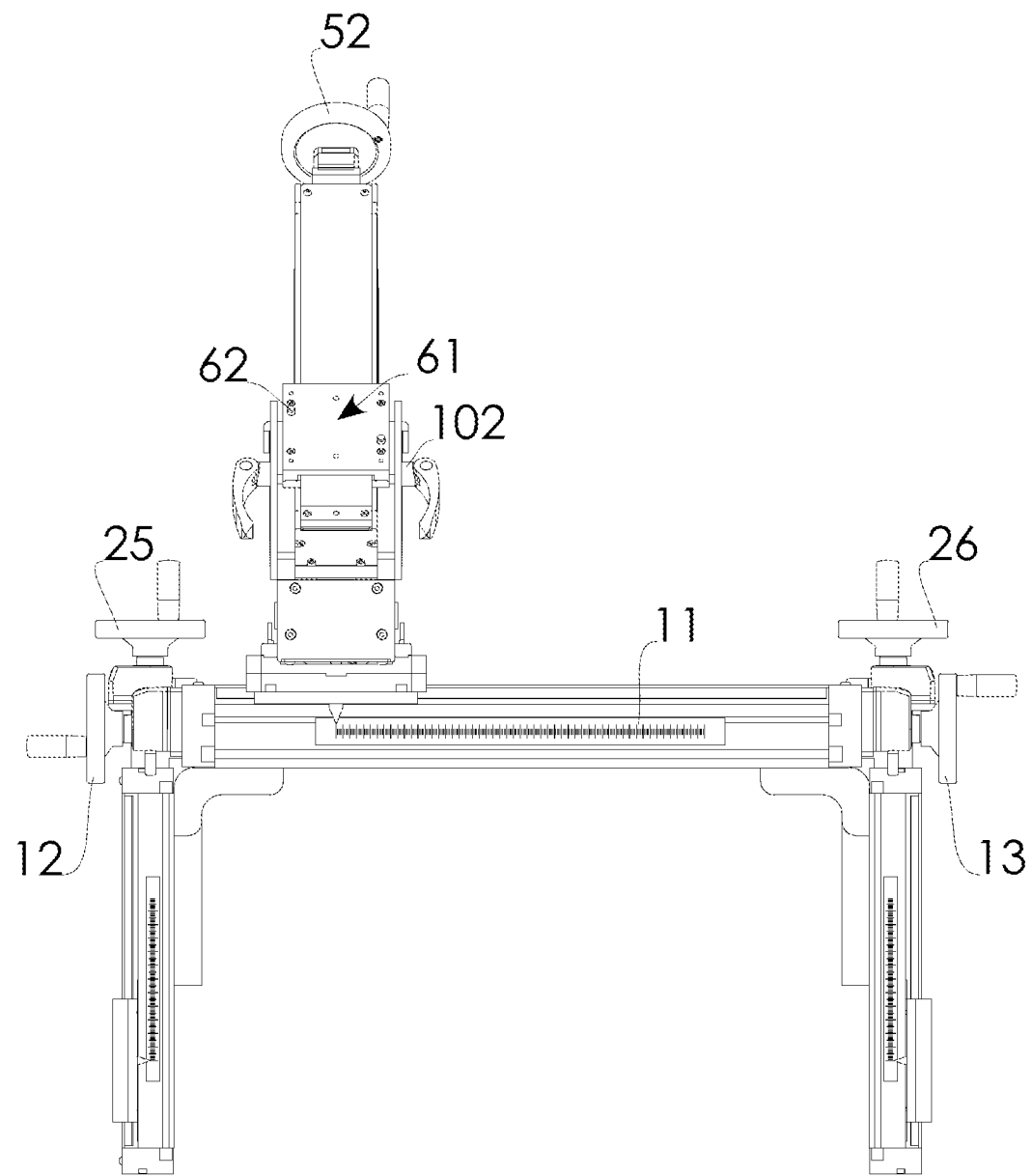
Figure 8:
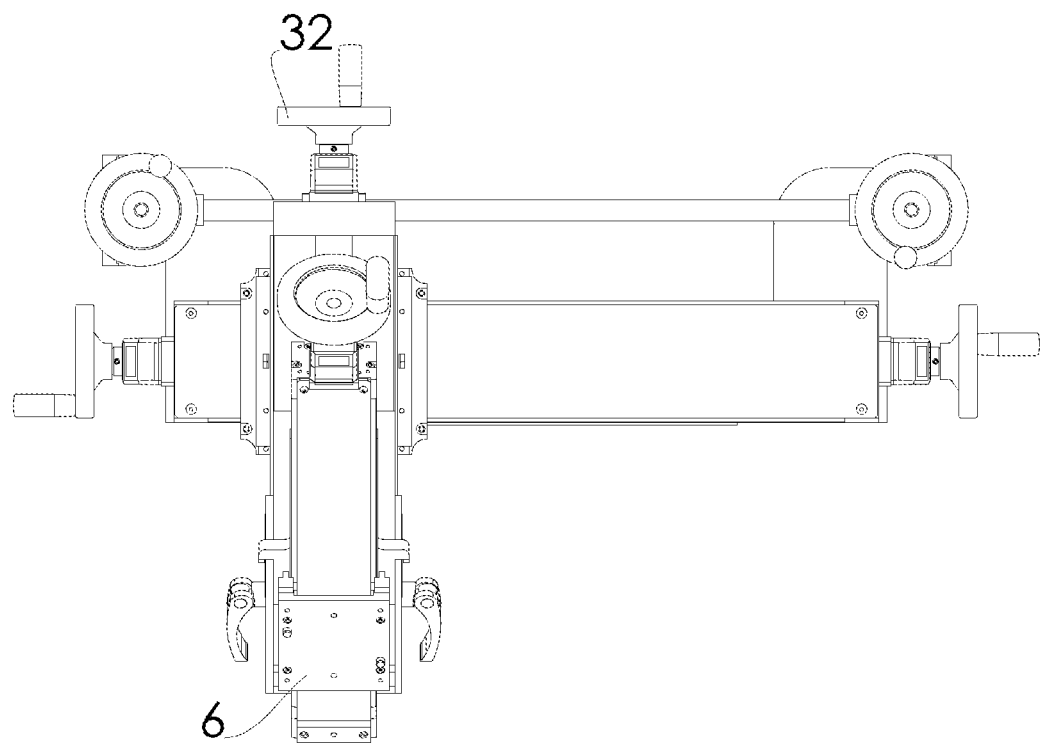
Figure 9:
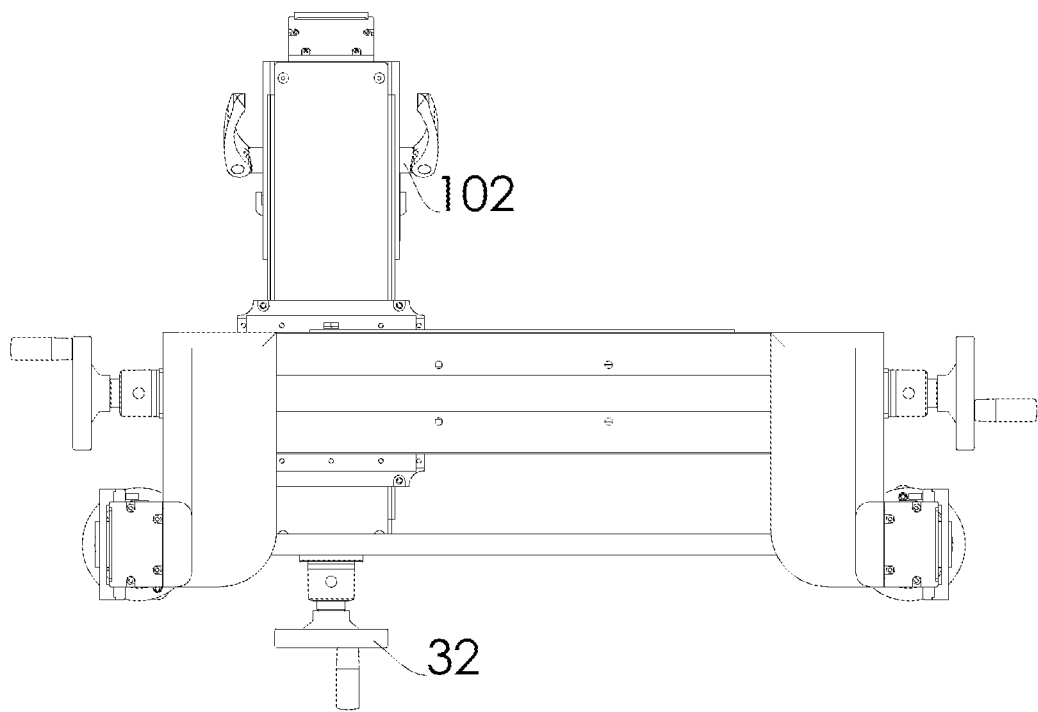

FIG. 7, FIG. 8, and FIG. 9 show a front, top, and bottom views respectively of the elements depicted in the two previous figures. Alignment pivots (62) are visible on the mutual engagement surface (61) of the turret (6).

Figure 10:
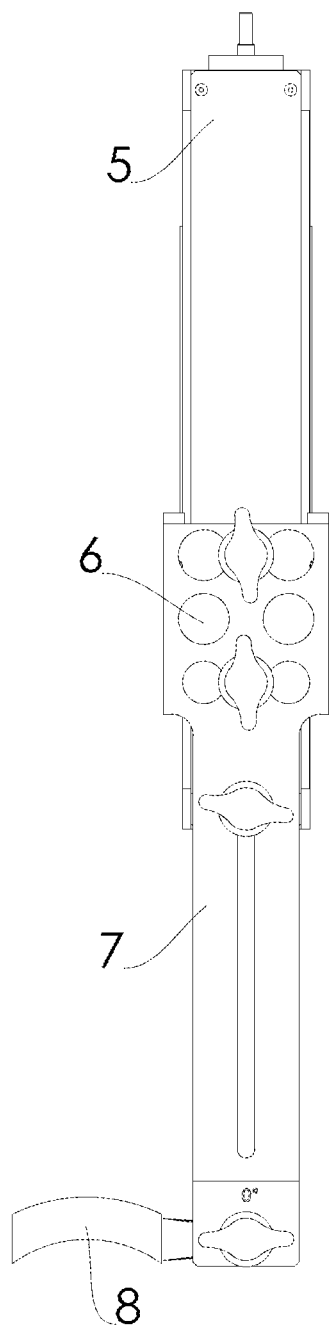
Figure 11:
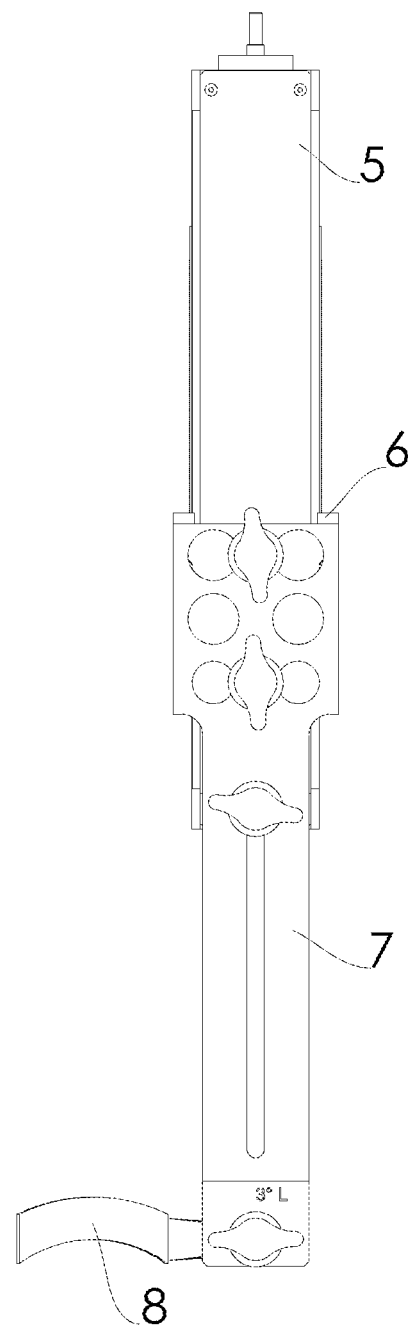
Figure 12:
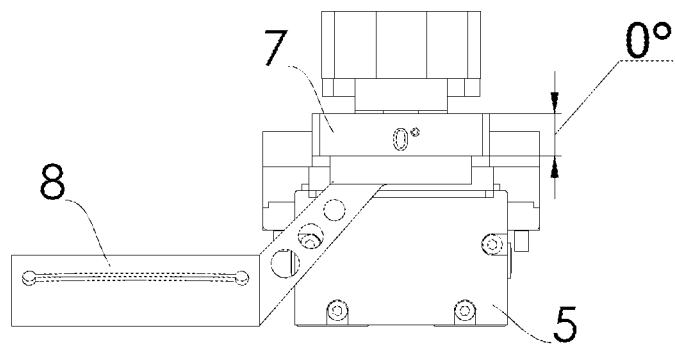
Figure 13:
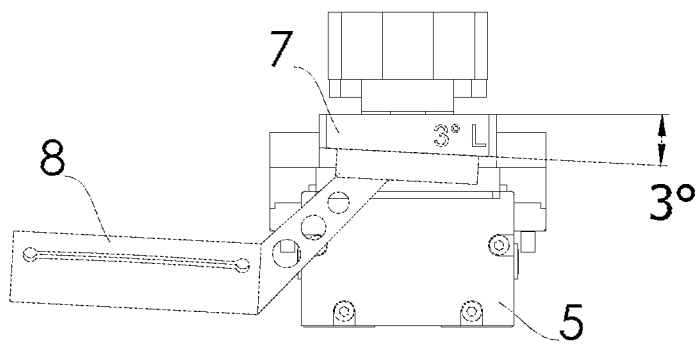

FIG. 10, FIG. 12, and FIG. 11 show, together with FIG. 13, two different instrument-holder arms (7), secured to the tool-holder turret (6) by way of two screws, which offer different inclinations of the engagement surface (72) to the surgical instrument (8), the positioning is done by reference pins.

Figure 14:
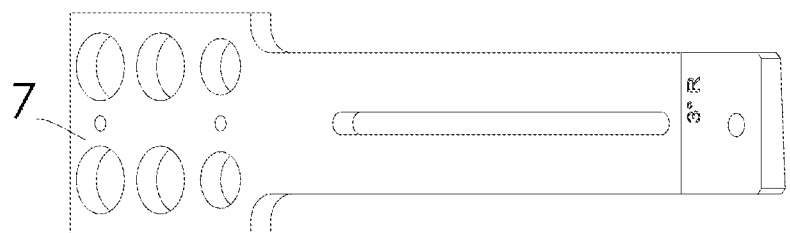
Figure 15:
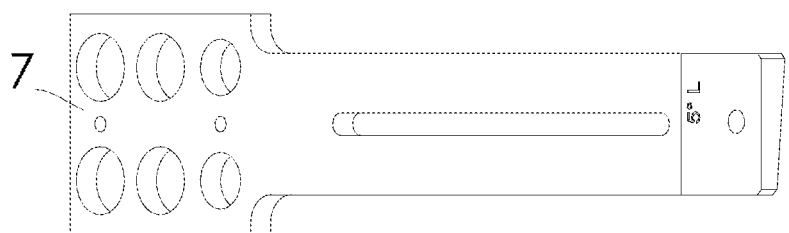
Figure 24:
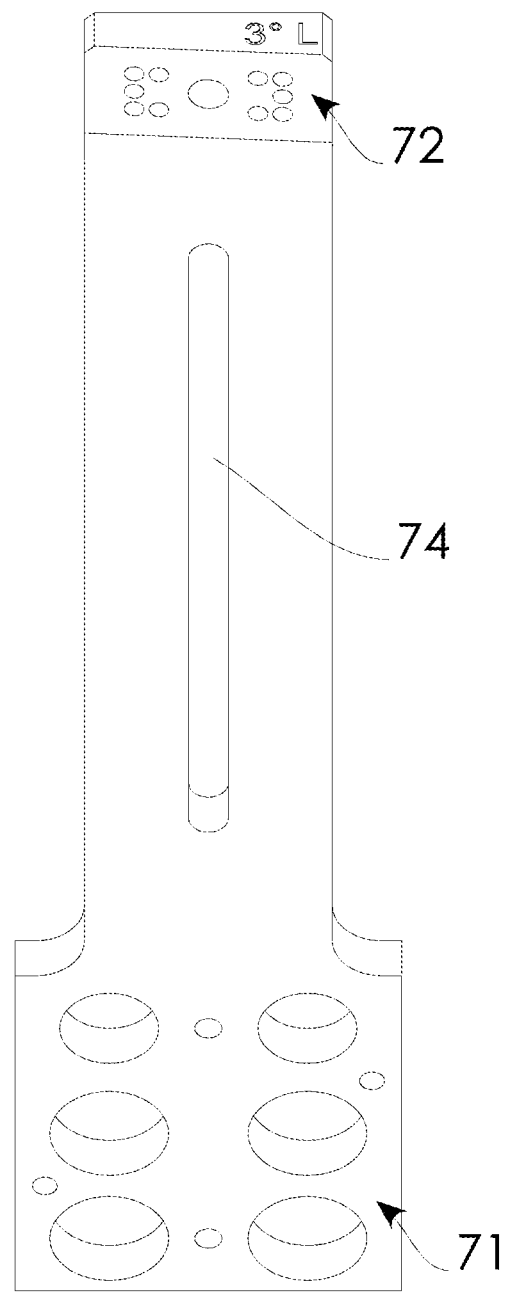

FIG. 14, FIG. 15, and FIG. 24 show three instrument-holder arms (7) inclined by 3 degrees to the right, 5 degrees to the left and 3 degrees to the left, respectively.

Figure 16:
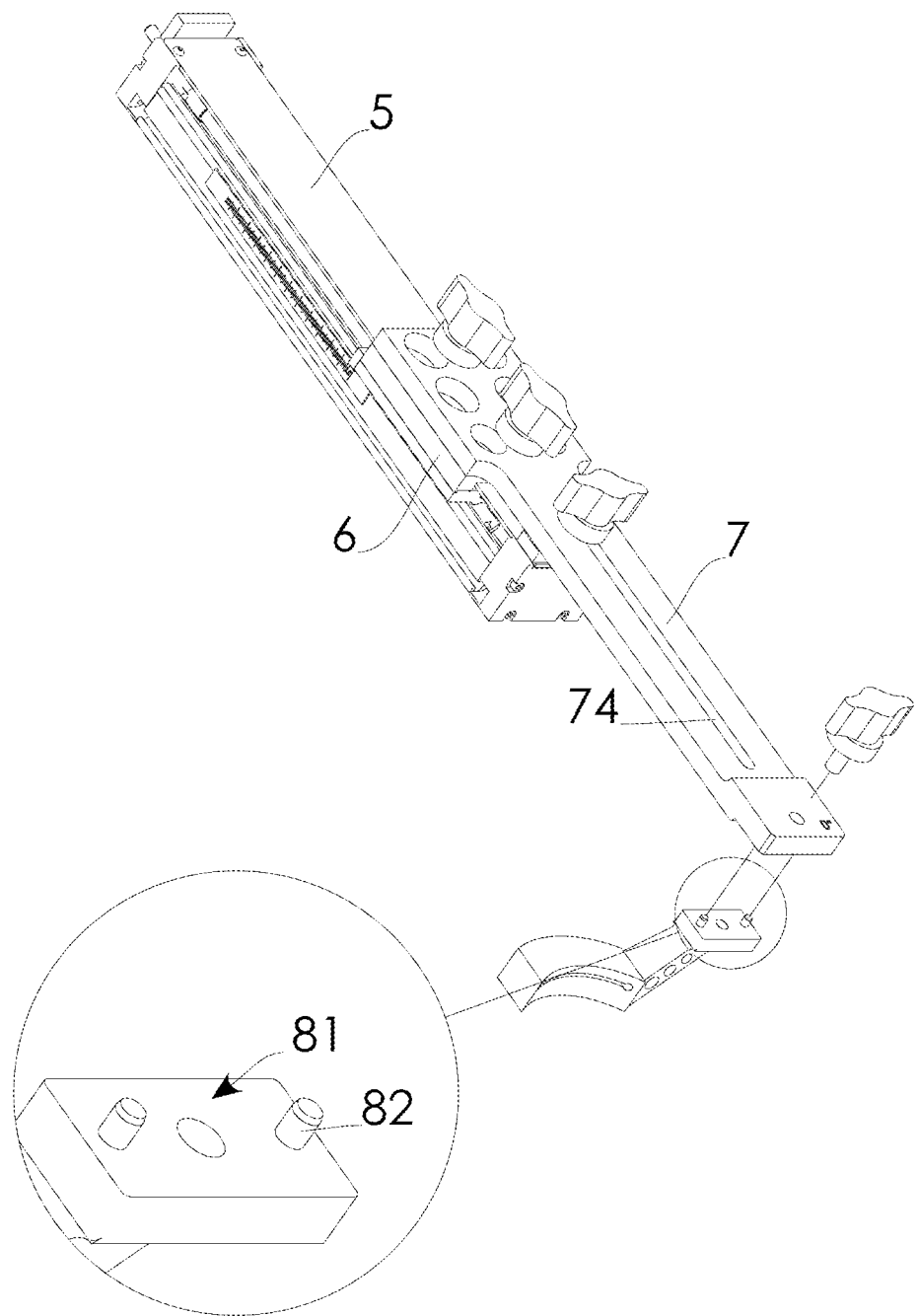
Figure 17:
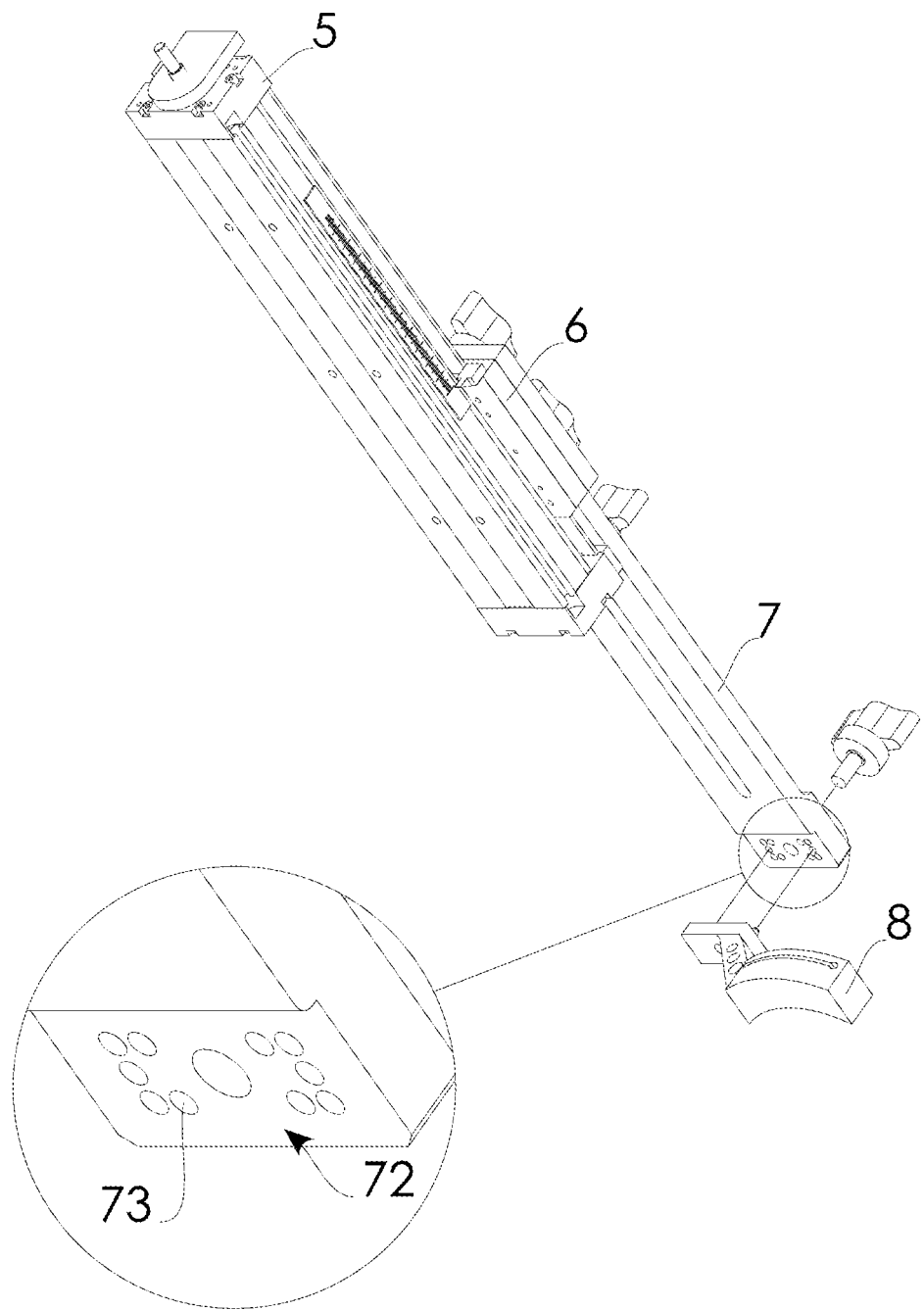

FIG. 16 and FIG. 17 show the coupling of the engagement surface (81) of the resection mask (8) with the engagement surface (72) of the instrument-holder arm (7) by way of a partial bottom and top axonometric views. The figures also show the alignment pivots (82) and the alignment holes (73) which guarantee a correct coupling besides its accuracy. The engagement surfaces are held in contact by a quick release screw. It is also appreciated that said instrument-holder arm (7) includes a longitudinal slot (74) in which a pivot integral with said reclining guide (5) shall slide.

FIG. 18 thru 23 are top and bottom views of different embodiments of the resection mask (8).

DETAILED DESCRIPTION OF ONE EMBODIMENT OF THE INVENTION

According to one preferred embodiment, the device according to the present patent application comprises a horizontal transversal linear bench (1) which vertically moves with respect to a base (9), thanks to the interposition of two vertical linear guides (21, 22), synchronized to each other; in the solution here shown, the guides are connected to the two ends of the bench (1) and are synchronized to each other in order to keep the bench (1) permanently horizontal; it is possible to use one guide only if the bench (1) is cantilevered.

A plate (4) slides along the axis (Y) of the bench (1), and a board (3) slides on said plate (4) along a longitudinal axis (X); a reclining guide (5), on which a turret (6) slides according to an axis of forward moving (W) of its own, is rotationally connected to the board (3) according to a transversal axis (Y').

A specific instrument-holder arm (7) is associated with the tool-holder turret (6) according to the actual requirement of the operating program. The instrument-holder arms (7) and the tool-holder turret (6) comprise mutual engagement means which make them reversibly integral; in particular, their mutual engagement surfaces (61, 71) comprise centering pins and reversible quick locking means.

In the embodiment depicted in the attached figures, the mutual engagement means comprise quick fasteners and a plurality of pins and holes so as to provide for a correct alignment between the individual elements.

In order to exploit all of its capabilities, the device shall be equipped with a plurality of instrument-holder arms (7), in each of which the engagement surface (72) between the arm and the surgical instrument is inclined differently, in order to mount the surgical piece of equipment or instrument at different inclinations; the surgical piece or equipment of instrument features an engagement surface (81) for associating with its corresponding engagement surface (72) of the instrument-holder arm.

The base (9) is either integral with the end of the plane (A) of the operating table corresponding to the patient's feet, or it seats directly on the ground, by way of adjustable feet (91).

The device comprises means for reciprocally moving and locking the individual elements that make it up and means for measuring the relative displacements between the base (9) and the guide (21, 22), between the bench (1) and the plate (4), between the plate (4) and the board (3), between the board (3) and the reclining guide (5), and between the reclining guide (5) and the turret (6).

In manufacturing the present device, it is convenient to assemble an angular guide and a plurality of linear guides with each other; in the linear guides, according to a preferred embodiment, the sliding between the carriage and the rail guide of each linear guide takes place by way of a ball recirculating screw manually driven by way of a handwheel. The two vertical guides (21, 22) are driven synchronously by way of motion transmission means, hence the vertical translation of bench (1) is obtained by acting on the control handwheel (25, 26) of either vertical guide (21, 22), at will.

The pieces of equipment are associated with the instrument-holder arm (7) by way of two pins and one quick fastener. Advantageously all resection masks feature the same distance between the center of the mask and the fixing center to the instrument-holder arm (7), so that every mask is positioned with the same coordinate, thus guaranteeing alignment to the mechanical axis in any situations.

The invention claimed is:

1. A support, positioning and handling device for surgical equipment and instruments, for arthroplasty operations on a patient who lays on a horizontal longitudinal plane, comprising:
    a horizontal transversal bench, slidingly coupled with said plane according to at least one vertical axis, a movable plate being slidable along an axis of said bench, wherein a board is slidingly coupled with said movable plate according to a longitudinal axis;
    a reclining guide being rotationally connected to said board according to a transversal axis; and
    a tool-holder turret being slidable on said reclining guide, wherein the device comprises means for measuring displacement and locking of the horizontal transversal bench, the movable plate, the board, the reclining guide and the tool-holder turret in intermediate positions,
    wherein said tool-holder turret is reversibly connected to a first end of at least one instrument-holder arm, wherein a second end of the at least one instrument-holder arm includes a surface for engaging at least one surgical piece of equipment or instrument,
    wherein said device comprises an angular guide which includes a fixed portion integral with said board and a movable portion which rotates with respect to said transversal axis, said movable portion of said angular guide being integrally connected to said reclining guide;
    wherein a vertical displacement of said bench takes place by way of two vertical guides, synchronized to each other, each of said guides being connected to an end of said bench,
    wherein further mutual engagement surfaces of said tool-holder turret and of said at least one instrument-holder arm comprise centering pins and reversible quick fastening means,
    wherein further the at least one instrument-holder arm includes a longitudinal slot in which a pivot integral with said reclining guide slides, and
    wherein further the device comprises means for a mutual displacement of the horizontal transversal bench, the movable plate, the board, the reclining guide and the tool-holder turret.

2. The support, positioning and handling device for surgical equipment and instruments according to claim 1 comprising a plurality of instrument-holder arms, wherein the surface for engaging at least one surgical piece of equipment or instrument of each of said instrument-holder arms is arranged according to a different angle from the other instrument-holder arms.

3. The support, positioning and handling device for surgical equipment and instruments according to claim 1 wherein said means for a mutual displacement comprise one or several ball recirculating screws driven by a respective handwheel.

4. The support, positioning and handling device for surgical equipment and instruments according to claim 3 comprising a plurality of instrument-holder arms, wherein the surface for engaging at least one surgical piece of equipment or instrument of each of said instrument-holder arms is arranged according to a different angle from the other instrument-holder arms.

5. The support, positioning and handling device for surgical equipment and instruments according to claim 3 wherein said means for a mutual displacement comprise actuators.

6. The support, positioning and handling device for surgical equipment and instruments according to claim 5 comprising a plurality of instrument-holder arms, wherein the surface for engaging at least one surgical piece of equipment or instrument of each of said instrument-holder arms is arranged according to a different angle from the other instrument-holder arms.

7. The support, positioning and handling device for surgical equipment and instruments according to claim 5 wherein a synchronization between said two vertical guides takes place by way of a means for motion transmission.

8. The support, positioning and handling device for surgical equipment and instruments according to claim 7 comprising a plurality of instrument-holder arms, wherein the surface for engaging at least one surgical piece of equipment or instrument of each of said instrument-holder arms is arranged according to a different angle from the other instrument-holder arms.

9. The support, positioning and handling device for surgical equipment and instruments according to claim 3 wherein the synchronization between said two vertical guides takes place by way of a means for motion transmission.

10. The support, positioning and handling device for surgical equipment and instruments according to claim 9 comprising a plurality of instrument-holder arms, wherein the surface for engaging at least one surgical piece of equipment or instrument of each of said instrument-holder arms is arranged according to a different angle from the other instrument-holder arms.

11. The support, positioning and handling device for surgical equipment and instruments according to claim 1 wherein said means for a mutual displacement comprise actuators.

12. The support, positioning and handling device for surgical equipment and instruments according to claim 11 comprising a plurality of instrument-holder arms, wherein the surface for engaging at least one surgical piece of equipment or instrument of each of said instrument-holder arms is arranged according to a different angle from the other instrument-holder arms.

13. The support, positioning and handling device for surgical equipment and instruments according to claim 1 wherein a synchronization between said two vertical guides takes place by way of a means for motion transmission.

14. The support, positioning and handling device for surgical equipment and instruments according to claim 13 comprising a plurality of instrument-holder arms, wherein the surface for engaging at least one surgical piece of equipment or instrument of each of said instrument-holder arms is arranged according to a different angle from the other instrument-holder arms.

* * * * *